United States Patent [19]

Wu

[11] Patent Number: 5,180,848

[45] Date of Patent: Jan. 19, 1993

[54] SYNTHESIS OF PHOSPHINOACETIC ACIDS

[75] Inventor: An-hsiang Wu, Bartlesville, Okla.

[73] Assignee: Phillips Petroleum Company, Bartlesville, Okla.

[21] Appl. No.: 788,909

[22] Filed: Nov. 7, 1991

[51] Int. Cl.$^5$ .......................... C07C 53/00; C07C 3/00
[52] U.S. Cl. .................................... 562/405; 562/512; 648/239
[58] Field of Search ................... 562/405, 512; 560/8, 560/129, 125

[56] References Cited

FOREIGN PATENT DOCUMENTS 0731742 11/1982 U.S.S.R. .............................. 562/512
1016292 5/1983 U.S.S.R. .............................. 562/405

OTHER PUBLICATIONS

K. Issleib and G. Thomas, "Darstellung von Carboxyphosphinen R$_2$P[CH$_2$]$_n$—CO$_2$H", Chem. Berichte 93, 1960, pp. 803–808.

M. A. Kakli et al., "The Preparation and Characterization of Some Phosphinoacetic Acids, Salts, and Esters", Syn. React. Inorg. Metal-Org. (Chem. 5, 1975, 357–371.

T. Jarolim et al., "Coordinating Behaviour of Diphenylphosphineacetic Acid", J. Inorg. Nucl. Chem., 38, 1976, pp. 125–129.

M. Peuckert and W. Keim, "A New Nickel Complex for the Oligomerization of Ethylene", Organometallics 1983, 2, pp. 594–597.

*Primary Examiner*—José G. Dees
*Assistant Examiner*—Keith MacMillan
*Attorney, Agent, or Firm*—K. K. Brandes

[57] ABSTRACT

P,P-dihydrocarbylphosphinoacetic acids are prepared by reacting a 2-methyl-4,4-dialkyl-2-oxazoline (preferably 2,4,4-trimethyl-2-oxazoline) with a basic alkali metal compound (preferably potassium hydride), followed by coupling with at least one halodihydrocarbylphosphine (preferably chlorodiphenylphosphine or chlorodiethylphosphine or chlorodi(t-butyl)phosphine or chlorodicyclohexylphosphine), and subsequent hydrolysis under acidic conditions.

21 Claims, No Drawings

SYNTHESIS OF PHOSPHINOACETIC ACIDS

BACKGROUND OF THE INVENTION

This invention relates to the synthesis of P,P-dihydrocarbylphosphinoacetic acids, which are useful as intermediates in the preparation of ethylene oligomerization catalysts. In one particular aspect, this invention relates to the preparation of P,P-diarylphosphinoacetic acid. In another particular aspect, this invention relates to the preparation of P,P-dialkylphosphinoacetic acids. In a further particular aspect, this invention relates to the preparation of P,P-dicycloalkylphosphinoacetic acids.

P,P-disubstituted phosphinoacetic acids of the type $R_2P-CH_2-CO_2H$ are known, and their preparation has been described in Chemische Berichte 93, 1960, pages 803-808. The preparation method described in this article comprises the steps of reacting a dihydrocarbyl-substituted alkali metal phosphide, e.g., $KP(C_6H_5)_2$, with a haloacetate, e.g., ethyl chloroacetate, and hydrolyzing the formed dihydrocarbylphosphinoacetic acid ester with an alcoholic sodium hydroxide solution and thereafter with sulfuric acid. This prior art synthesis requires the use of very reactive alkali metal phosphides. The present invention is directed to a less dangerous, more practical synthesis of P,P-dihydrocarbylphosphinoacetic acids which does not involve the use of alkali metal phosphides.

SUMMARY OF THE INVENTION

It is an object of this invention to prepare P,P-dihydrocarbylphosphinoacetic acids. It is a particular object of this invention to prepare P,P-diarylphosphinoacetic acids. It is another particular object of this invention to prepare P,P-dialkylphosphinoacetic acids. It is a further particular object of this invention to prepare P,P-dicycloalkylphosphinoacetic acids. Other objects and advantages will be apparent from the detailed description of the invention and the appended claims.

In accordance with this invention, a process for preparing at least one P,P-dihydrocarbylphosphinoacetic acid comprises the steps of:

(a) reacting at least one 2-methyl-4,4-dialkyl-2-oxazoline, wherein each of the two alkyl groups can contain 1-6 carbon atoms, with at least one basic compound of the general formula MZ, wherein M is an alkali metal and Z is selected for the group consisting of —H, —OR', —NH$_2$, —NHR' and —N(R')$_2$, with each R' being an alkyl or cycloalkyl group having 1-8 carbon atoms, at a temperature not to exceed about 0° C. for a time period of at least about 1 second;

(b) adding to the reaction mixture obtained in step (a), at a temperature not to exceed about 0° C., at least one halodihydrocarbylphosphine having the general formula of $R_2PX$, wherein X is Cl or Br or I, and each R is selected from the group consisting of alkyl groups containing 1-10 carbon atoms, cycloalkyl groups containing 3-10 carbon atoms and aryl groups containing 6-12 carbon atoms;

(c) heating the mixture obtained in step (b) to a temperature of above about 0° C. and maintaining the mixture at that temperature for a period of time of at least about 1 minute;

(d) contacting the reaction mixture obtained in step (c) with at least one mineral acid under such conditions as to form said at least one P,P-dihydrocarbylphosphinoacetic acid; and (e) recovering said P,P-dihydrocarbylphosphinoacetic acid from the reaction mixture obtained in step (d).

In a preferred embodiment, the 2-methyl-4,4-dialkyl-2-oxazoline is 2,4,4-trimethyl-2-oxazoline. In another preferred embodiment the basic compound used in step (a) is an alkali metal hydride, MH, as defined above.

DETAILED DESCRIPTION OF THE INVENTION

The reagents which are used in the process of this invention are known. They are either commercially available or can be prepared by known methods. 2-methyl-4,4-dialkyl-2-oxazolines having the general formula of

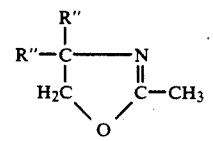

can be prepared by the reaction of acetic acid with a 2-amino-1-alkanol of the general formula $H_2N-C(R''))_2-CH_2-OH$, wherein each R'' is independently selected from the groups consisting of alkyl groups containing 1-6 carbon atoms. Preferably, acetic acid is reacted with 2-amino-2-methyl-1-propanol, $H_2N-C(CH_3)_2-CH_2-OH$, so as to form 2,4,4-trimethyl-2-oxazoline, which is also commercially available from Vertizon Chemical Company, Houston, TX.

The basic compounds of the general formula MZ, as defined above, are well known, and can be prepared by reaction of an alkali metal with either $H_2$ or an alcohol or ammonia or an amine. The preferred basic compound is potassium hydride (KH) which is commercially available from Pfaltz & Bauer, Stamford, CT.

Halodihydrocarbylphosphines can be prepared by the reaction of a phosphorous trihalide (in particular $PCl_3$) with 2 equivalents of a hydrocarbylmagnesium halide (in particular an alkylmagnesium chloride or alkylmagnesium bromide). Preferred chlorodialkylphosphines, such as chlorodiethylphosphine, chlorodi(t-butyl)phosphine, chlorodicyclohexylphosphine and chlorodiphenylphosphine, are commercially available, e.g., from Strem Chemicals, Inc., Newburyport, MA. Other examples of suitable halohydrocarbylphosphines include fluorodimethylphosphine, chlorodimethylphosphine, bromodimethylphosphine, iodadimethylphosphine, fluorodiethylphosphine, bromodiethylphosphine, iododiethylphosphine, chlorodipropylphosphine, chlorodi(n-butyl)phosphine, chlorodiphenylphosphine, chlorodihexylphosphine, chloromethylethylphosphine (and other mixed haloalkylphosphines), fluorodicyclopentylphosphine, chlorodicyclopentylphosphine, bromodicyclopentylphosphine, iododicyclopentylphosphine, fluorodicyclohexylphosphine, bromodicyclohexylphosphine, iodocyclohexylphosphine, fluorodiphylphosphine, bromodiphenylphosphine, iododiphenylphosphine, fluoroditolyphosphine, chloroditolyphosphine, bromoditolylphosphine, iododitolyphosphine and the like, and mixtures of any of the above compounds.

Step (a) of the process of this invention is carried out under such conditions as to replace one H atom of the methyl group in the 2 position of 2-methyl-4,4-dialkyl-2-oxazoline with an alkali metal. The reaction temperature in step (a) generally is in the range of about −80° C. to about 0° C. (preferably about −80° C. to about −60° C.). The reaction time generally ranges from about 1 second to about 1 hour, preferably about 10–40 minutes. Generally, the molar ratio of the alkali metal compound MZ (defined above) to the 2-methyl-4,4-dialkyl-2-oxazoline is in the range of about 1:1 to about 2:1. Preferably, both reagents are dissolved in a suitable solvent (such as an ether).

Step (b) of the process of this invention is carried out in any suitable order at a low temperature, preferably in the range of about −80° C. to about 0° C., more preferably about −80° C. to about −60° C. Generally, the halodihydrocarbylphosphine is added to the reaction mixture obtained in step (a) with agitation, preferably within a time period of about 0.1 minute to about 30 minutes, more preferably within a time period of about 1–15 minutes. Generally, the molar ratio of the added halodihydrocarbylphosphine to the 2-methyl-4,4-dialkyl-2-oxazoline employed in step (a) is approximately 0.9:1 to about 1.2:1.

In step (c), the mixture obtained in step (b) is heated, generally with agitation (stirring), to a temperature above about 0° C., preferably to about 10°–40° C., and agitated at this temperature for a time period sufficient to substantially replace the alkali metal in the intermediate species formed in step (b) with the —PR$_2$ group, while alkali metal halide is formed as a by-product. Generally, step (c) is carried out for a period of time in the range of about 1 minute to about 120 minutes, preferably for about 10–50 minutes.

In step (d) of the process of this invention, the intermediate compound formed in step (c) is hydrolyzed to the P,P-dihydrocarbylphosphinoacetic acid by heating (generally with agitation) with an aqueous solution of at least one mineral acid, preferably HCl or H$_2$SO$_4$ or HNO$_3$ or mixtures thereof, preferably an acid solution having a normality of about 0.5–5. Generally, the pH of the reaction mixture in step (d) is about 0–4, the reaction temperature is in the range of about 60° to 100° C., and the reaction time is about 5 to 60 minutes. The by-product of the hydrolysis reaction of step (d) is believed to be an ammonium compound, such as HO—CH$_2$—C(R″)$_2$—NH$_3$Cl, when the employed acid is HCl.

Recovery step (e) can be carried out in any suitable manner after the completed reaction mixture of step (d) has been cooled (preferably to about 10°–30° C.). Preferably, the formed P,P-dihydrocarbylphosphinoacetic acid is extracted from the completed reaction mixture with a suitable solvent, preferably an ether or any other effective solvent which is substantially immiscible in water, followed by evaporation of the solvent. The thus obtained crystalline P,P-dihydrocarbylphosphinoacetic acid can be further purified by dissolving it in an aqueous alkali metal hydroxide solution, followed by acidification with one of the above-mentioned mineral acids, so as to precipitate the purified P,P-dihydrocarbylphisphinoacetic acid, which is subsequently separated from the acidic solution (e.g., by filtration), as described in the example below.

The hydrocarbyl groups in the produced P,P-dihydrocarbylphosphinoacetic acid are the same as the R groups defined above for the halodihydrocarbylphosphine, i.e., alkyl groups with 1-10 carbon atoms or cycloalkyl groups containing 3-10 carbon atoms and aryl groups containing 6-10 carbon atoms. Preferred P,P-dihydrocarbylphosphinoacetic acids are dimethylphosphinoacetic acid, diethylphosphinoacetic acid, methylethylphosphinoacetic acid, dipropylphosphinoacetic acid, di(n-butyl)phosphinoacetic acid, di(t-butyl)phosphinoacetic acid, dicyclohexylphosphinoacetic acid, diphenylphosphinoacetic acid, ditolyphosphinoacetic acid, and the like.

The following example is presented to further illustrate the invention and is not to be contrued as unduly limiting the scope of this invention.

Example

This example illustrates the preparation of various dihydrocarbylphosphinoacetic acids from 2,2,4-trimethyl-2-oxazoline in accordance with the present invention. Essentially all lab-grade reagents used in the preparations described in this example had been supplied by Aldrich Chemical Company, a subsidiary of Sigma-Aldrich Corporation, Milwaukee, WI.

A solution of 1.13 g (10 millimols) of 2,2,4-trimethyl-2-oxazoline in 10 mL of dry tetrahydrofuran was added, within a period of 10 minutes, to a well agitated suspension of 0.46 g (11.5 millimols) of dry, pure potassium hydride in 10 mL of dry tetrahydrofuran, while maintaining a temperature of −78° C. by cooling the reaction mixture with an external dry ice/acetone cold bath. After the addition of the 2,2,4-trimethyl-2-oxazoline had been completed, this first reaction mixture was stirred for 30 minutes, at about −78° C. Thereafter, 10 millimols of chlorodiphenylphosphine were added by means of a syringe to the cold reaction mixture during a time period of 5 minutes. After the addition of chlorodiphenylphosphine had been completed, this second reaction mixture was stirred for 5 more minutes, at about −78° C., and was then allowed to warm to room temperature (by removing the external cold bath). After this second reaction mixture had been stirred for 30 minutes at room temperature, 40 mL of an aqueous 3 normal HCl solution was added, followed by heating the acidified reaction mixture under reflux conditions for about 15-20 minutes and subsequent cooling to room temperature.

The cooled acidified reaction mixture was extracted three times with 40 mL of diethyl ether. The three organic layers containing the ether solvent and crude diphenylphosphinoacetic acid were combined, dried over anhydroous MgSO$_4$, filtered and subjected to vacuum evaporation. The residue of this vacuum evaporation, i.e., crude diphenylphosphineoacetic acid, was dissolved in 30 mL of a 10 weight percent aqueous KOH solution. This alkaline solution was heated at 70°-80° C. for 15 minutes, cooled and washed three times with 40 mL of diethyl ether. To the aqueous solution (containing the potassium salt of diphenylphosphinoacetic acid) was slowly added enough of 38% aqueous hydrochloric acid, at a temperature of about 0° C., to acidify the solution, which was then filtered, so as to yield white, microcrystalline diphenylphosphinoacetic acid, which had a melting point of 220° C. The yield of diphenylphosphinoacetic acid, based on the weight of chlorodiphenylphosphine, was 76%.

Additional preparations in accordance with the above-described procedure were carried out with chlorodicyclohexylphosphine, chlorodi(tertiary-butyl)phosphine and chlorodiethylphosphine, respectively, in lieu of chlorodiphenylphosphine, thus producing dicyclohexylphosphinoacetic acid (melting point: 85° C.) at a yield of 72%, di(tertiary-butyl)phosphinoacetic acid (melting point: 71° C.) at a yield of 70%, and diethylphosphinoacetic acid (melting point: 96° C.) at a yield of 78%, respectively.

Reasonable variations, modifications and adaptations, for various conditions can be made within the scope of the disclosure and the appended claims, without departing from the scope of the invention.

That which is claimed is:

1. A process for preparing at least one P,P-dihydrocarbylphosphinoacetic acid comprising the steps of:
   (a) reacting at least one 2-methyl-4,4-dialkyl-2-oxazoline, wherein each of the two alkyl groups can contain 1-6 carbon atoms, with at least one basic compound of the formula MZ, wherein M is an alkali metal and Z is selected from the group consisting of —H, —OR', —NH$_2$, —NHR' and —N(R')$_2$, with R' being an alkyl or cycloalkyl group having 1-8 carbon atoms, at a temperature not to exceed about 0° C. for a time period of at least about 1 second;
   (b) adding to the reaction mixture obtained in step (a), at a temperature not to exceed about 0° C., at least one halodihydrocarbylphosphine having the general formula R$_2$PX, wherein X is Cl or Br or I, and each R is selected from the group consisting of alkyl groups containing 1-10 carbon atoms, cycloalkyl groups containing 3-10 carbon atoms and aryl groups containing 6-12 carbon atoms;
   (c) heating the mixture obtained in step (b) to a temperature of above about 0° C. and maintaining the mixture at that temperature for a time of at least about 1 minute;
   (d) contacting the reaction mixture obtained in step (c) with at least one mineral acid under such conditions as to form said at least one P,P-dihydrocarbylphosphinoacetic acid; and
   (e) recovering said at least one P,P-dihydrocarbylphosphinoacetic acid from the reaction mixture obtained in step (d).

2. A process in accordance with claim 1, wherein said at least one 2-methyl-4,4-dialkyl-2-oxazoline is 2,4,4-trimethyl-2-oxazoline.

3. A process in accordance with claim 1, wherein said at least one basic compound is at least one alkali metal hydride.

4. A process in accordance with claim 1, wherein said at least one 2-methyl-4,4-dialkyl-2-oxazoline is 2,4,4-trimethyl-2-oxazoline and said at least one basic compound is potassium hydride.

5. A process in accordance with claim 1, wherein step (a) is carried out at at temperature in the range of about −80° C. to about 0° C. for a period of time in the range of about 1 second to about 1 hour.

6. A process in accordance with claim 1, wherein step (a) is carried out at a temperature in the range of about −80° C. to about −60° C. for a period of time of about 10-40 minutes.

7. A process in accordance with claim 1, wherein step (a) is carried out at a molar ratio of said at least one basic compound to said at least one 2-methyl-4,4-dialkyl-2-oxazoline in the range of about 1:1 to about 2:1.

8. A process in accordance with claim 1, wherein said at least one halodihydrocarbylphosphine used in step (b) is at least one chlorodihydrocarbylphosphine.

9. A process in accordance with claim 1, wherein said at least one halodihydrocarbylphosphine used in step (b) is chlorodiphenylphosphine, and said at least one P,P-dihydrocarbylphosphinoacetic acid formed in step (d) and recovered in step (e) is P,P-diphenylphosphinoacetic acid.

10. A process in accordance with claim 9, wherein said at least one 2-methyl-4,4-dialkyl-2-oxazoline is 2,4,4-trimethyl-2-oxazoline and said at least one basic compound is potassium hydride.

11. A process in accordance with claim 1, wherein said at least one halodihydrocarbylphosphine used in step (b) is chlorodiethylphosphine, and said at least one P,P-dihydrocarbylphosphinoacetic acid formed in step (d) and recovered in step (e) is P,P-diethylphosphinoacetic acid.

12. A process in accordance with claim 11, wherein said at least one 2-methyl-4,4-dialkyl-2-oxazoline is 2,4,4-trimethyl-2-oxazoline and said at least one basic compound is potassium hydride.

13. A process in accordance with claim 1, wherein said at least one halodihydrocarbylphosphine used in step (b) is chlorodi(tertiary-butyl)phosphine, and said at least one P,P-dihydrocarbylphosphinoacetic acid formed in step (d) and recovered in step (e) is P,P-di(tertiary-butyl)phosphinoacetic acid.

14. A process in accordance with claim 13, wherein said at least one 2-methyl-4,4-dialkyl-2-oxazoline is 2,4,4-trimethyl-2-oxazoline and said at least one basic compound is potassium hydride.

15. A process in accordance with claim 1, wherein said at least one halodihydrocarbylphosphine used in step (b) is chlorodicyclohexylphosphine, and said at least one P,P-dihydrocarbylphosphinoacetic acid formed in step (d) and recovered in step (e) is P,P-dicyclohexylphosphinoacetic acid.

16. A process in accordance with claim 15, wherein said at least one 2-methyl-4,4-dialkyl-2-oxazoline is 2,4,4-trimethyl-2-oxazoline and said at least one basic compound is potassium hydride.

17. A process in accordance with claim 1, wherein step (c) is carried out at a temperature of about 10°-40° C. for about 1-120 minutes.

18. A process in accordance with claim 1, wherein step (d) is carried out with an aqueous solution of said at least one mineral acid selected from the group consisting of HCl, HNO$_3$ and H$_2$SO$_4$.

19. A process in accordance with claim 18, wherein said aqueous solution of said at least one mineral acid has a normality of about 0.5-5.

20. A process in accordance with claim 18, wherein step (d) is carried out at a temperature of about 60°-100° C. for about 5-60 minutes.

21. A process in accordance with claim 1, wherein the at least one P,P-dihydrocarbylphosphinoacetic acid obtained in step (d) is purified by dissolving it in an aqueous alkali metal hydroxide solution, acidifying the obtained alkaline solution so as to precipitate said at least one P,P-dihydrocarbylphosphinoacetic acid, and recovering the at least one precipitated P,P-dihydrocarbylphosphinoacetic acid.

* * * * *